United States Patent
Canstein et al.

(10) Patent No.: US 9,089,308 B2
(45) Date of Patent: Jul. 28, 2015

(54) METHOD FOR PROCESSING MEASUREMENT DATA FROM PERFUSION COMPUTER TOMOGRAPHY

(75) Inventors: Christian Canstein, Erlangen (DE); Hendrik Ditt, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 741 days.

(21) Appl. No.: 12/778,165

(22) Filed: May 12, 2010

(65) Prior Publication Data

US 2010/0290686 A1    Nov. 18, 2010

(30) Foreign Application Priority Data

May 14, 2009   (DE) .................... 10 2009 021 234

(51) Int. Cl.
| | | |
|---|---|---|
| G06K 9/00 | (2006.01) | |
| A61B 6/00 | (2006.01) | |
| G06T 7/20 | (2006.01) | |

(52) U.S. Cl.
CPC ............... *A61B 6/504* (2013.01); *A61B 6/481* (2013.01); *A61B 6/501* (2013.01); *A61B 6/507* (2013.01); *G06T 7/2006* (2013.01); *G06T 2207/10081* (2013.01); *G06T 2207/30104* (2013.01)

(58) Field of Classification Search
CPC .......................... G06T 7/0012; G06T 7/2006
USPC ........................................................ 382/131
See application file for complete search history.

(56) References Cited

U.S. PATENT DOCUMENTS

| | | | | |
|---|---|---|---|---|
| 5,970,182 A | * | 10/1999 | Goris | 382/278 |
| 6,512,807 B1 | * | 1/2003 | Pohlman et al. | 378/4 |
| 6,745,066 B1 | * | 6/2004 | Lin et al. | 600/425 |
| 8,103,076 B2 | * | 1/2012 | Larson et al. | 382/130 |
| 2005/0110791 A1 | * | 5/2005 | Krishnamoorthy et al. | 345/419 |
| 2007/0016016 A1 | * | 1/2007 | Haras et al. | 600/431 |
| 2009/0016587 A1 | * | 1/2009 | Strobel et al. | 382/130 |
| 2009/0028409 A1 | * | 1/2009 | Tsukagoshi et al. | 382/131 |

OTHER PUBLICATIONS

Kenneth A. Miles und M. R. Griffiths; Perfusion CT: a worthwhile enhancement? Miles et al.; The British Journal of Radiology, Apr. 2003, Seiten 220 bis 231; Magazine; 2003.
P.Montes u. G.Lauritsch, "Noise Reduction by Temporal Estimation in Perfusion Computed Tomography", IEEE Nuclear Science Symposium Conference Record, 2005, M11-372, S.2747-2751; Others.
German Office Action for Priority Doc DE 10 2009 021 234.5.

* cited by examiner

*Primary Examiner* — Sheetal R Paulson
(74) *Attorney, Agent, or Firm* — Harness, Dickey & Pierce, P.L.C.

(57) ABSTRACT

A method is disclosed for processing measurement data from perfusion computed tomography, in which both perfusion parameters, in order to calculate which arterial and venous TACs are generated, and dynamic CTA images are generated from the measurement data. In at least one embodiment of the proposed method, averaging is performed over the dynamic CTA images from a plurality of temporally successive time phases in order to obtain averaged CTA images, wherein the time phases over which averaging is performed are determined from the arterial or venous TAC(s). In some cases, the method can dispense with an additional static CTA and so the amount of the injected contrast agent and the radiation dose can be reduced.

10 Claims, 1 Drawing Sheet

METHOD FOR PROCESSING MEASUREMENT DATA FROM PERFUSION COMPUTER TOMOGRAPHY

PRIORITY STATEMENT

The present application hereby claims priority under 35 U.S.C. §119 on German patent application number DE 10 2009 021 234.5 filed May 14, 2009, the entire contents of which are hereby incorporated herein by reference.

FIELD

At least one embodiment of the present invention generally relates to a method for processing measurement data from perfusion computed tomography, preferably one in which both perfusion parameters, in order to calculate which arterial and venous TACs (time-attenuation curves) are generated, and dynamic CTA images are calculated from the measurement data. At least one embodiment of the invention also generally relates to a data processing system for executing the method.

BACKGROUND

It is generally of interest in computed tomography (CT) examinations to keep both the amount of injected contrast agent and the radiation dose to a minimum so that the patient is not exposed to unnecessary stresses. However, this often cannot be achieved just like that. Thus, for example, when examining stroke patients using computed tomography, two further CT scans are generally performed with administration of contrast agent after a native CT scan.

Here, this is a dynamic perfusion measurement and a subsequent CT angiography (CTA). In the case of the dynamic perfusion measurement, use is made of an injection protocol with a high flow rate of at least 5 ml/s for the contrast agent in order to produce a short, sharp contrast agent bolus, which is a precondition for calculating perfusion parameters such as blood flow and blood volume.

In CT angiography, a contrast-agent injection protocol is used that produces a longer, wider contrast agent bolus. Here, a larger overall amount of contrast agent is used and the flow rate is lower. This leads to more regular enrichment of the contrast agent in the vessels and longer vessel sections being able to be illustrated in the angiography. The CT angiography is used to be able to determine the origin of a perfusion disorder. The two last-mentioned examinations lead to a significant amount of contrast agent injected into the patient and to a high radiation dose to which the patient is exposed.

Relatively new techniques in computed tomography, such as the so-called adaptive 4D spiral (A4DS) from Siemens allow perfusion measurements in the skull that are no longer limited by the width of the detector to a few layers, but which can be carried out in the entire skull volume with a cover of up to 10 cm. The measurement data from such a perfusion computed tomography scan can be used not only for calculating perfusion parameters, but also for generating dynamic CT angiographies, which illustrate the inflow and outflow of the contrast agent in the vessels. Such a dynamic angiography however cannot replace the conventional static CT angiography because in each time phase, illustrated by the dynamic angiography, only a short vessel section is enriched with contrast agent due to the short contrast agent bolus.

US 2009/0028409 A1 discloses a method for processing measurement data from perfusion computed tomography as per the preamble of patent claim 1. In this document, blood vessels are extracted by way of a thresholding technique.

US 2007/0016016 A1 describes inter alia a method for processing measurement data from perfusion computed tomography, in which an image is obtained from the data records from a dynamic CT angiography by way of MIP over the entire period of time or an averaged image is obtained by averaging. P. Montes and G. Lauritsch: "Noise Reduction by Temporal Estimation in Perfusion Computed Tomography", in: IEEE Nuclear Science Symposium Conference Record, 2005, M11-372, pages 2747-2751, describe techniques for reducing noise in perfusion computed tomography, wherein one refinement carries out temporal smoothing in order to improve the signal-to-noise ratio. The smoothing is brought about for example by the use of a suitable low-pass filter.

SUMMARY

In at least one embodiment of the present invention, a method is disclosed by which a subsequent static CT angiography for illustrating vessels can be dispensed with in many cases when performing perfusion computed tomography and which allows unambiguous identification of bone and/or vessel voxels for segmentation.

A method is disclosed, in at least one embodiment, for processing measurement data from perfusion computed tomography. Advantageous refinements of the method are the subject matter of the dependent patent claims or can be gathered from the following description and the example embodiment.

The method, in at least one embodiment, generates arterial and venous TACs from the measurement data in a known fashion and uses these to calculate perfusion parameters of a tissue, more particularly of the brain tissue. The measurement data is also used to generate dynamic CTA images. The method is distinguished by virtue of the fact that averaging is performed in each case over a plurality of CTA images from temporally successive time phases in order to obtain one or more averaged CTA image(s). Here, the temporally successive time phases for averaging are determined from the arterial and/or venous TACs. The time phase is understood to be the period of time of the underlying individual contrast agent scan which constitutes a state of contrast agent influx. Together with the preceding and subsequent contrast agent scans, it is possible to illustrate the influx and washout of the contrast agent in the vessels in a dynamic fashion if said scans are shown in succession as a film. This is referred to as dynamic CT angiography.

It goes without saying that perfusion parameters corresponding to the utilized perfusion software are generally generated and displayed to the user in addition to the arterial and venous TACs. The averaged CTA image(s) is or are also visualized on an image-display apparatus in a suitable fashion.

Processing measurement data in order to generate perfusion parameters is known from the prior art of such perfusion measurements. For this, a number of commercially available software packages can already be used. For example, K. A. Miles et al., "Perfusion CT: A worthwhile enhancement?", The British Journal of Radiology, 76 (2003), 220 to 231, the entire contents of which are hereby incorporated herein by reference, provide an overview of available perfusion methods that are also commercially available in software packages. Here, TACs can be calculated voxel-by-voxel or averaged over predetermined regions. Similarly, the calculation of CTA images from computed tomography measurement data recorded within the scope of CT angiography is known and so this does not have to be discussed in any more detail here.

The present method of at least one embodiment, now averages over a plurality of CTA images from temporally successive time phases in order thereby to increase the region enriched with contrast agent in the displayed image or the displayed images. This obtains an impression of the image like the CTA image from static CTA. For this, the information from the arterial or venous TACs is used in which the maximum of the arterial or venous contrast-agent enrichment is evident in each case.

In order to generate an arterially-weighted CTA image, averaging is then performed over time phases that lie around the maximum of the arterial TAC. In order to generate a venous-weighted CTA image, averaging is performed over time phases that lie around the maximum of the venous TAC. For an arterial-venous weighted CTA image, averaging is performed over time phases lying around and between the two maximums. In this fashion, optimum image results are respectively obtained for the averaging. Here, averaging is not understood exclusively as the formation of an average value from a plurality of image data or measurement data, but also as pure addition of this data.

In an advantageous refinement, the number of time phases over which averaging is performed can be selected as a function of the gradient of the increase or decay of the respective arterial or venous TAC. In the case of a steeper increase or decay, averaging is performed over a lower number of time phases than in the case of a flatter increase or decay. Hence, this adaptive selection of the number of time phases to be averaged takes into account the time resolution such that despite averaging a relatively high time resolution is also achieved in the case of high temporal dynamics of the contrast agent flow. The time phases over which averaging is performed can, like the selection of the number thereof for averaging, be selected automatically by a processing program that evaluates the respective TACs in a suitable fashion. In order to select the number of time phases, this program must be able to access a table or a function linking this number to the gradient of the respective TAC.

In a further refinement, an averaged CTA image is generated not only for the time phases in the region of the maximum of the respective TAC but rather additional averaged CTA images are generated by averaging over time phases before and/or after the respective maximum. In time phases in which the TAC has a flat profile, for example significantly behind the maximum, it is also possible, for example, to average over a larger number of time phases than in the region of the maximum.

Averaging over the dynamic CTA images of a plurality of time phases has the additional advantage of improving the image quality even in a time-resolved display. For example, if an averaged image of e.g. three successive time phases is illustrated in each case rather than illustrating the dynamic CTA images from individual time phases, this obtains a softer display and an improved signal-to-noise ratio. Such averaged CTA images can for example be visualized in temporal succession on an image-display apparatus. Preferably, the number of time phases over which averaging is performed can be adjusted interactively in the process by a user. As a result of this, the user can in each case set the optimum ratio of desired time resolution and image quality, depending on the clinical problem and the available data.

The proposed method of at least one embodiment, can also be used to generate arterial, venous and arterial-venous vessel displays from the volume perfusion data, i.e. from the measurement data from the perfusion computed tomography, which displays correspond to the display from a conventional static CTA or are at least very similar. Here, the method cleverly uses results, particularly the TACs, which are generated in any case in a volume perfusion measurement by way of computed tomography.

In stroke examinations where it is certain that no vessel pathology outside of the skull region scanned by the perfusion computed tomography scan is the cause of a perfusion disorder, the method can dispense with a separately carried out static CTA. This reduces both the amount of injected contrast agent and the radiation dose compared to a conventional examination, and the examination duration in the CT scanner is also reduced, which is very important in stroke examinations in particular. Unlike the display of the individual time phases of a dynamic CTA, the optimized vessel illustrations of the CTA images averaged according to the method show the vessels in a fashion customary to the user from conventional static CTA images. The short contrast agent bolus of the perfusion computed tomography is stretched, so to speak. Compared to the individual time phases of dynamic CTA, the averaging over a plurality of phases moreover improves the signal-to-noise ratio, both for the arterial, venous and arterial-venous vessel displays generated thus and also for the vessel displays optimized by averaging.

In at least one embodiment of the proposed method for processing measurement data from perfusion computed tomography, temporal information is used for segmenting or removing the bones from the averaged or dynamic CTA data record. Since bones and contrast-enhanced vessels often have very similar HU values, the distinction that has to be made between bones and vessels in order to remove the bones from a CTA data record can often not be made unambiguously in conventional CT angiography.

In at least one embodiment of the proposed refinement, the HU information of each individual voxel over time is used to obtain an unambiguous distinction between voxels representing bones and voxels representing vessels in a dynamic, registered CTA data record. If there is a significant change in the HU value of the voxel over a plurality of time phases, this is due to the influx and washout of the contrast agent and the voxel is part of a vessel. By contrast, if the HU values of the voxel do not change, or only vary slightly, this is unambiguously a bone voxel. Here, the maximum variation interval of the HU values for assigning the corresponding voxel to a bone is prescribed by the user. This technique can be used not only for unambiguously detecting bone voxels and removing the latter, but also for unambiguously identifying vessel voxels, for example for segmenting the vascular tree.

In an advantageous development of the proposed method for processing measurement data from perfusion computed tomography, the time-resolved CTA data is also used for calculating functional parameters of the vessels. This allows determination of additional information relating to vessel pathologies, more particularly dynamic parameters like the parameters obtained by Doppler sonography or phase-contrast magnetic resonance imaging. For this, respectively one TAC is determined for each pixel within the vessel either as in perfusion measurements, or a TAC is determined for e.g. a plurality of vessel pixels in a layer, i.e. the TAC is averaged. Further parameters can then be determined from these TACs, such as the height of a peak (maximum), the width of the peak (FWHM—full width half maximum), the time difference between the arterial curve and the venous curve in 2 different vessels, the distance between the arterial and venous maximum, the gradient of the respective curves, the integral over the arterial or venous curve, the number of peaks etc. These parameters can be illustrated in color on the vessels like the perfusion parameter displays or alternatively can be visualized in the form of a diagram, e.g. the height of the arterial peak as a function of the position along the vessel center line, and thus supply potentially clinically relevant information in addition to the pure vessel geometry.

In refinements of the proposed method, the measurement data or the images of the individual time phases are registered. Such registration is already brought about automatically by commercially available perfusion software because this is also a precondition for calculating the perfusion parameters. In the skull, the vessels are relatively static and only move a little during the flow cycle and so good registration of the vessels in the various successive time phases is possible here. In general, a rigid registration technique is used for this.

The technique of distinguishing bone voxels and vessel voxels on the basis of the temporal development of the HU values used in the method obtains unambiguous separation of bone and vessel voxels, even in the problematic areas of the base of a skull. This technique can also serve as the basis for the vessel segmentation. By calculating the vessel parameters on the basis of the dynamic CTA images, information relating to the vessel function is also obtained in addition to the pure vessel geometry. Thus, the measurement data from perfusion computed tomography can be used to display not only the cause of the pathology, e.g. a stenosis, but potentially the effect on the flow function as well, e.g. a changed gradient in the TAC curve.

The proposed method of at least one embodiment is executed on a data processing system, which in a known fashion has at least one computational processor, memory and corresponding interfaces for data input and data output. Here, the data processing system comprises one or more programs that execute the individual method steps for processing the imported or stored measurement data as per the proposed method. Such a data processing system can be directly connected to a computed tomography scanner in order to be able to display the results on an image-display apparatus directly after the perfusion computed tomography scan.

BRIEF DESCRIPTION OF THE DRAWINGS

In the following text, an embodiment of the proposed method is once again explained briefly in conjunction with the drawings, in which.

DETAILED DESCRIPTION OF THE EXAMPLE EMBODIMENTS

Figure 1:
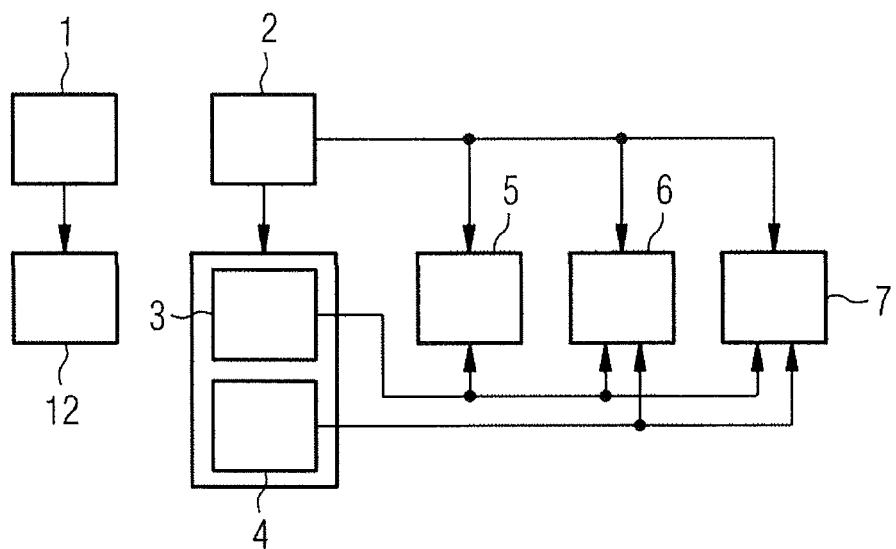
FIG. 1 shows a schematic illustration of a workflow for carrying out an embodiment of the proposed method and FIG. 2 shows an example of TACs calculated in an embodiment of the method.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an example of the workflow when examining a stroke patient using computed tomography. Herein, a native CT scan 1 is carried out at first in order to recognize bleeding in the region of the skull (elimination of bleeding 12). Subsequently, there is a volume perfusion computed tomography scan 2 as per an embodiment of the proposed method. The measurement data from this perfusion CT scan 2 is used to firstly generate arterial and venous TACs 4 after registering 3 the individual phases. Naturally, perfusion parameters are also calculated herein. In the present example, the measurement data from the perfusion CT scan 2 is also used to calculate time-resolved (dynamic) CTA images 5, arterially- and venous-weighted CTA images 6 and functional parameters of the vessels (functional CTA 7). This affords the possibility of dispensing with a subsequent static CTA provided that the cause of the perfusion disorder lies within the volume region covered by the perfusion CT scan 2.

Figure 2:
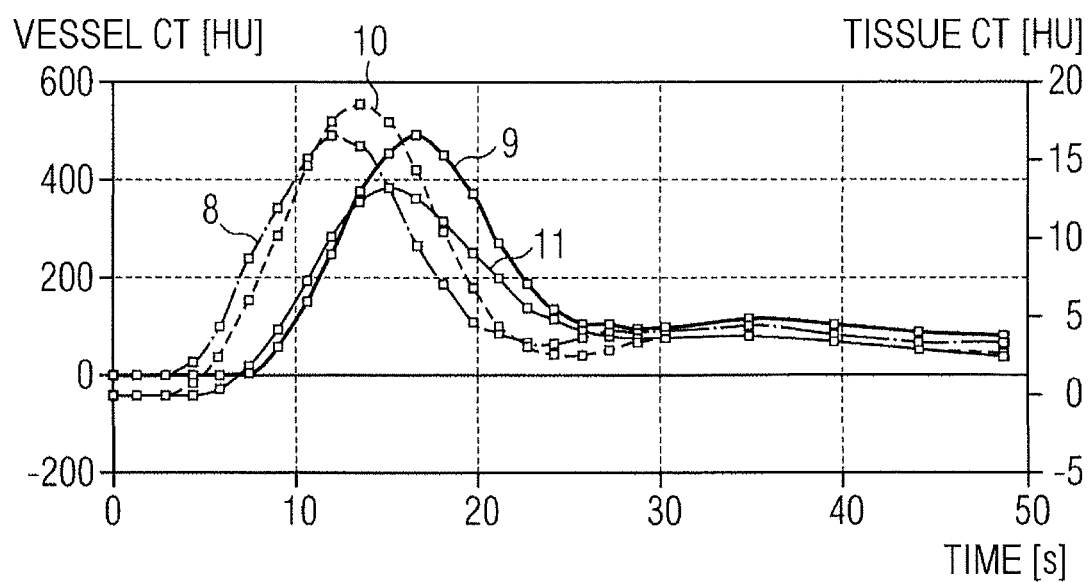

FIG. 2 shows an example of an arterial 8 and venous TAC 9, as are generated automatically during the evaluation of the measurement data from the perfusion computed tomography scan. Furthermore, this image illustrates the TACs for the tissue of the left 10 and right brain half 11, which TACs are likewise generated automatically. This information is used in the present method for selecting the time phases for averaging the CTA images. These TACs provide the information relating to what time phases ideally have to be added for an arterial vessel illustration, what time phases ideally have to be added for a venous vessel illustration and what time phases ideally have to be added for an arterial-venous vessel illustration. Thus, for example, the maximum of the arterial TAC 8 is at time phase 12. For an optimized arterial vessel illustration, it is then possible, for example, to add the CTA images from time phases 10 to 14.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for processing measurement data from perfusion computed tomography (CT), comprising:
    calculating perfusion parameters and at least one dynamic CT-angiography image from the measurement data, the measurement data being gathered by an Adaptive 4D CT scanner such that a same one of the measurement data gathered at a same time is used to calculate both the perfusion parameters and the dynamic CT-angiography image, the dynamic CT-angiography image associated with a short vessel section and the perfusion parameters used to calculate which arterial and venous time attention curves are generated;
    for each of the calculating perfusion parameters and the calculating the at least one dynamic CT-angiography image, averaging, in each case over a plurality of dynamic CT-angiography images from temporally successive time phases, to obtain one or more averaged CT-angiography image such that the one or more averaged CT angiography images are associated with a longer vessel section than the dynamic CT-angiography image, the temporally successive time phases for averaging being determined from the at least one time-attenuation curve; and distinguishing between voxels representing bones and voxels representing vessels by:
  determining a change in time of a Hounsfield Unit (HU) value of a respective voxel over a number of time phases and at least one of:
    assigning voxels of the at least one dynamic or the at least one averaged CT-angiography images without variation in the HU value or voxels with only one variation in the HU value lying within an interval to the bones, and
    assigning voxels with a variation in the HU value lying above an interval to the vessels.

2. The method as claimed in claim 1, wherein the averaging is performed over time phases for generating an arterially-weighted CT-angiography image that lie around a maximum of the arterial time-attenuation curve.

3. The method as claimed in claim 1, wherein the averaging is performed over time phases for generating a venous-weighted CT-angiography image that lie around a maximum of the venous time-attenuation curve.

4. The method as claimed in claim 1, wherein the number of time phases over which averaging is performed is selected as a function of a gradient of the increase or decay of the respective time-attenuation curve, and wherein averaging is performed over a lower number of time phases in the case of a steeper increase or decay than in a case of a flatter increase or decay.

5. The method as claimed in claim 4, wherein the number of time phases is selected automatically by a processing program.

6. The method as claimed in claim 1, wherein, in order to generate CT-angiography images with an improved image quality, averaging is performed over time phases that lie around a maximum of the at least one of venous and arterial time-attenuation curve, wherein the number of time phases over which averaging is performed is interactively adjustable.

7. The method as claimed in claim 1, wherein, in order to generate further averaged CT-angiography images, averaging is also performed over respectively successive time phases before and after the maximum of the time-attenuation curves, wherein the obtained images are illustrated in temporal succession.

8. The method as claimed in claim 1, wherein time-attenuation curves of vessels are determined from the dynamic CT-angiography images and functional parameters of the vessels are calculated from said curves.

9. The method as claimed in claim 8, wherein one or more parameters in an image display of the dynamic CT-angiography images are visualized as colored representations of the vessels or in a separate diagrammatic illustration.

10. A non-transitory computer readable medium comprising:
program segments that, when executed on a computer device, cause the computer device to implement a method of processing measurement data from perfusion computed tomography (CT) that includes:
  calculating perfusion parameters and at least one dynamic CT-angiography image from the measurement data, the measurement data being gathered by an Adaptive 4D CT scanner such that a same one of the measurement data gathered at a same time is used to calculate both the perfusion parameters and the dynamic CT-angiography image, the dynamic CT-angiography image associated with a short vessel section and the perfusion parameters used to calculate which arterial and venous time attention curves are generated;
  for each of the calculating perfusion parameters and the calculating the at least one dynamic CT-angiography image, averaging, in each case over a plurality of dynamic CT-angiography images from temporally successive time phases, to obtain one or more averaged CT-angiography image such that the one or more averaged CT angiography images are associated with a relatively longer vessel section than the dynamic CT-angiography image, the temporally successive time phases for averaging being determined from the at least one time-attenuation curve; and
  distinguishing between voxels representing bones and voxels representing vessels by:
    determining a change in time of a Hounsfield Unit (HU) value of a respective voxel over a number of time phases and at least one of:
      assigning voxels of the at least one dynamic or the at least one averaged CT-angiography images without variation in the HU value or voxels with only one variation in the HU value lying within an interval to the bones, and
      assigning voxels with a variation in the HU value lying above an interval to the vessels.

* * * * *